United States Patent [19]

Uzgiris

[11] Patent Number: 5,762,909
[45] Date of Patent: Jun. 9, 1998

[54] TUMOR TARGETING WITH POLYMERIC MOLECULES HAVING EXTENDED CONFORMATION

[75] Inventor: Egidijus Edward Uzgiris, Schenectady, N.Y.

[73] Assignee: General Electric Company, Schenectady, N.Y.

[21] Appl. No.: 691,164

[22] Filed: Aug. 1, 1996

Related U.S. Application Data

[63] Continuation-in-part of Ser. No. 521,767, Aug. 31, 1995, abandoned.

[51] Int. Cl.[6] .................. A61K 49/00; G01N 31/00; G01N 33/48
[52] U.S. Cl. .................. 424/9.34; 424/9.1; 424/9.3; 424/1.65
[58] Field of Search .................. 424/1.11, 1.37, 424/1.65, 1.69, 9.1, 9.3, 9.34, 9.4, 9.5; 530/300, 324–330; 430/944; 544/313; 534/10–16; 424/9.6

[56] References Cited

U.S. PATENT DOCUMENTS

| | | | |
|---|---|---|---|
| 4,855,353 | 8/1989 | Kurami et al. | 525/54.1 |
| 5,534,241 | 7/1996 | Torchilin et al. | 424/9.321 |
| 5,554,748 | 9/1996 | Sieving et al. | 540/465 |
| 5,593,658 | 1/1997 | Bogdanov et al. | 424/9.34 |

OTHER PUBLICATIONS

Uzgiris (Feb. 1995), Biophysical Journal, vol. 68, No. 2, Part 2, Abstract #442 "Effects of Charge and Conformation on Macromolecule Uptake by Tumors".

Shih et al (1988), Int. J. Cancer, vol. 41, pp. 832–839, "Site Specific Linkage of Methotrexate to Monoclonal Antibodies Using An Intermediate Carrier".

Rosenthal et al (1993), Investigative Radiology, vol. 28, No. 9, pp. 789–795, "The Demonstration of Human Tumors on Nude Mice Using Godolinium Labeled Monoclonal Antibodies for MR Imaging".

Pratesi et al (1985), J. Cancer, vol. 52, pp. 841–848, "Poly-L-Aspartic Acid as a Carrier for Doxorubicin Drug Comparative in vivo Study of Free and Polymer Bound Drug".

Sieving et al (1990), Bioconjugate Chem., vol. 1, No. 1, pp. 65–71 "Preparation and Characterization of Paramagnetic Polychelates and their Protein Conjugates".

Primm (1988), Critical Reviews in Therapeutic Drug Carrier Systems, vol. 5, No. 3, pp. 189–227, "Drug Monoclonal Antibody Conjugates for Cancer Therapy: Potentials and Limitations".

Opsahl et al (Mar. 1994), Biophysical Journal, vol. 66, No. 2, Part 2, Abstract #81, "Dynamics of NMR Contrast Agent Uptake by Tumors".

*Primary Examiner*—John Kight
*Assistant Examiner*—Dameron Jones
*Attorney, Agent, or Firm*—Lawrence P. Zale; Marvin Snyder

[57] ABSTRACT

Enhanced drug delivery to tumor tissue is obtained by attaching drug molecules to elongated polypeptide carrier molecules several orders of magnitude longer than wide. These are chosen to have a high net negative charge. The carrier molecules are created by unfolding long polypeptides by a large degree of substitution with steric hindrance molecules, such as diethylene triamine pentaacetic acid (DTPA) with at least 90% substitution. This causes the conformation to be worm-like as evidenced by a measure of persistence length, with a diameter small enough squeeze through the pore structures of tumor tissue but not so small as to pass through pores of vessels in normal tissue. The length is determined by optimizing two processes, blood circulation lifetime, and tumor uptake. The elongated conformation may cause the complex to become entwined with stroma in tumor interstitium and become trapped. The complex molecules provides increased therapeutic benefit in effecting tumor tissue destruction, or may be used in enhancing imaging contrast depending upon the active agent attached to the carrier molecules. The enhanced concentration and retention of the complex molecules within the tumor reduces side effects of the active agent in other tissues.

5 Claims, 3 Drawing Sheets

5,762,909

TUMOR TARGETING WITH POLYMERIC MOLECULES HAVING EXTENDED CONFORMATION

CROSS REFERENCE TO RELATED APPLICATIONS

This is a continuation-in-part of Ser. No. 08/521,767, abandoned filed Aug. 31, 1995.

BACKGROUND OF THE INVENTION

1. Field of the Invention

The present invention relates to medical treatment of tumor tissue, and more specifically, deals with optimizing drug delivery to tumor tissue as well as to the diagnostic imaging of tumors.

2. Description of Related Art

In many medical procedures it is important to accumulate a certain active agent to a desired tissue type. For example, in chemotherapy, it is important to deliver drugs only to cancerous tumor tissue, and not to normal tissue, since these drugs destroy the tissue with which they come in contact. Another example would be in medical imaging. Contrast agents are attached to carrier molecules which are specific to tumor tissue. As the carrier molecules concentrate in the tumor tissue, the contrast agents enhance a medical image of this tissue.

Typically targeting has been done using a carrier molecule in which the active agent, is attached and moves with the carrier molecule to the targeted tissue. "Poly-L-Aspartic Acid As a Carrier for Doxorubicin: A Comparative In vivo Study of Free and Polymer-bound Drugs" by G. Pratesi, G. Cavi, G. Pezzoni, O. Bellini, S. Penco, S. Tinelli and F. Zunino, *J. Cancer*, 52, pp. 841–848 describes the use of a chemotherapy drug attached to Poly-L-Aspartic Acid (PAA).

In another publication "Macromolecule-Drug Conjugates and Targeted Cancer Chemotherapy" by H. Sezaki, M. Hashida, *CRC Critical Reviews in Therapeutic Drug Carrier Systems* Vol. 1, Issue 1, pp. 1–39 also describes the use of macromolecule carriers which are attached to a chemotherapy drug used in targeting tumor tissue.

Many of the carrier molecules employed are proteins having a globular or folded configuration as evidenced by Table I of the Sezaki et al. paper.

In order to sufficiently concentrate an active agent riding on a carrier molecule, which will be referred to as a complex molecule, within tumor tissue, there are several requirements which must be met, which have been overlooked in the prior art. First, since pore size of blood vessels in tumor tissue is known to be significantly larger than the pore size of blood vessels in normal tissue, i.e., the permeability of tumor blood vessels to macromolecules is much higher than that of normal tissue blood vessels, the cross sectional size of the molecules is important in preventing entry of the complex into normal tissue but yet allowing entry into tumors.

Tumor tissue also differs from normal tissue by having fibrous strands, stroma, running throughout its interstitium. This interstitial matrix comprises a large fraction of the tumor tissue volume in many tumors.

Although macromolecules may enter tumor tissue, the molecules are not always able to penetrate into the interstitium of the tumor with sufficient concentration due to the resistance to diffusion provided by the extracellular matrix.

Currently there is a need for a more efficient method of concentrating an active agent in tumor tissue.

SUMMARY OF THE INVENTION

Highly substituted polypeptides having a diameter larger than pores of blood vessels of normal tissue and smaller than pores of blood vessels of tumor tissue, having a length several orders of magnitude greater than its diameter, and a net negative charge, form a worm-like chain conformation with a long persistence length, 100–600 Angstroms (Å). Active agents are attached to these carrier molecules to create carrier/active agent (C/A) complex molecules which are introduced into a blood vessel of the subject. These C/A complex molecules pass though the pores of only the tumor tissue and interact with the fibrous structures of the tumor interstitium. The uptake and retention of these molecules is more than five times higher than observed for other macromolecules such as compact peptide coils or globular proteins. The penetration of the tumor interstitium by the C/A complex molecules may be enhanced by the process of reptation in which the C/A molecules are chosen, or modified to have a worm-like configuration and can "snake" around fixed obstacles in the extracellular matrix of the tumor interstitium.

The optimum length of the carrier molecules is determined by multiplying a graph of lifetime within the blood vs. carrier length with a graph of uptake within the tumor vs. carrier length to result in a tumor uptake curve. A carrier polymer length is determined from the peak of this graph.

OBJECTS OF THE INVENTION

It is an object of the present invention to provide increased concentration of an active agent in tumor tissue of a subject relative to other tissue of the subject.

It is another object of the present invention to provide a method for selectively destroying tumor tissue within a subject.

It is another object to deliver therapeutic drugs to tumor tissue.

It is another object to deliver contrast agents to tumor tissue for the diagnostic imaging of tumors.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawing, in which:

DETAILED DESCRIPTION OF THE INVENTION

Figure 1:
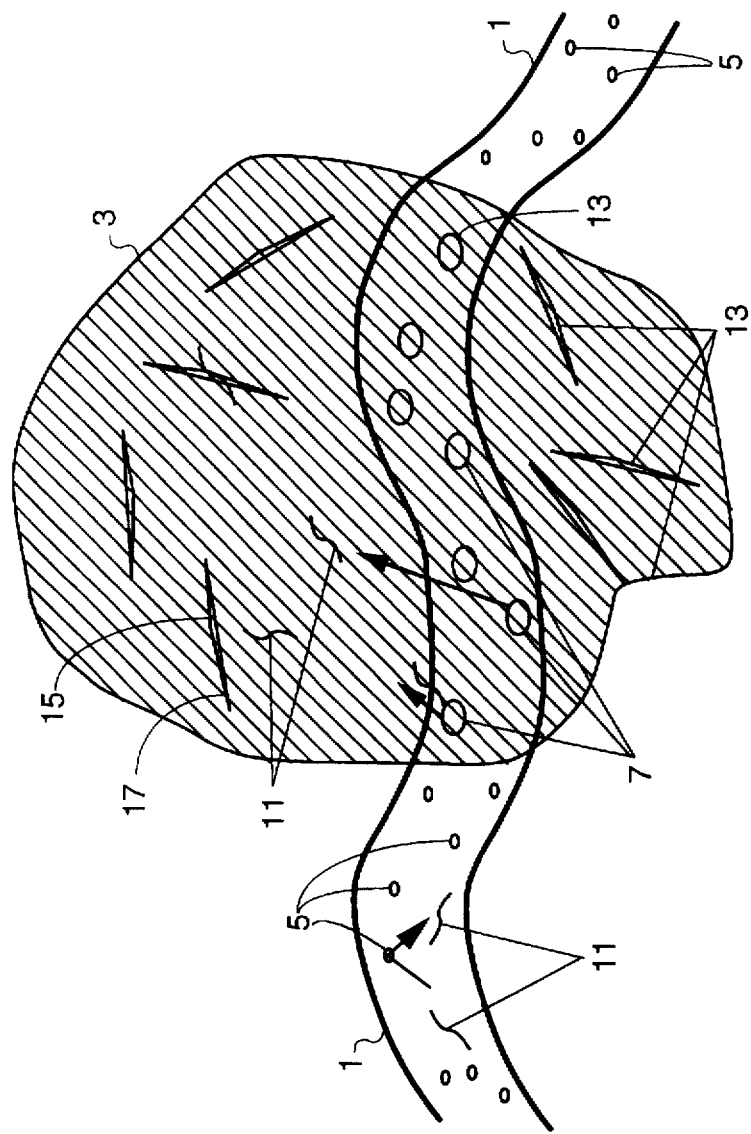
FIG. 1 is an illustration of the functioning of the present invention in a subject.

In FIG. 1 a blood vessel 1 is shown passing from normal tissue into tumor tissue 3. Pores 5 of blood vessels in the normal tissue are small and carrier/active agent (C/A) complex molecules 11 being a polypeptide carrier molecule attached to an active agent molecule, are contained in the vessels. The active agent molecules may be known image contrast enhancing agents, drugs, toxins, or other molecules which is intended to be targeted to the tumor tissue. Inside of tumor tissue 3, pores 7 are much larger than that of pores 5 in normal tissue. C/A complex molecule 13 is shown passing through pore 9, into the interstitial space of tumor 3.

Alternatively, the pores may not be simple channels but maybe backed by a fibrous network of the basement membrane of the endothelium. A process called reptation allows elongated worm-like molecules wiggle around obstacles, and to pass through restricted openings, but globular or coiled molecules would be unable to pass through. Experimental results described below suggest that a large fraction of tumor channels may in fact be restricted channels of this type rather than simple openings in the endothelium.

Stroma 17 is abundant in the interstitial space of tumor 3. C/A complex molecule 15, having the proper confirmation, size, and charge, is shown tangling with stroma 17 become entrapped in the interstitial space of tumor 3.

Cross-Sectional Diameter

It is therefore important that the C/A complex molecules have a cross sectional diameter which is larger than that of the pores of normal tissue such that they are contained within the blood vessels in normal tissue but have a cross sectional diameter smaller than that of the pores of the vessels in tumor tissue such that they may readily pass out of the pores and into the interstitial space. It was found during experimentation that complex molecules having a diameter of approximate 20–50 Angstroms (Å) generally pass through pore structures of the tumor tissue, but not that of normal tissue. (A C/A complex described in more detail later, highly substituted gadolinium diethylene triamine pentaacetic acid (Gd-DTPA) poly-L-lysine (PLL), which may be used in accordance with to the present invention, has a cross sectional diameter of about 25 Angstroms.)

Polymer Length

In order to be effective at concentrating within a tumor, the C/A complex molecules must also have a length long enough to increase the time in which they circulate in the blood, but small enough to be taken up in the tumor interstitium. Once in the tumor interstitium, longer molecules tend to remain there, possibly by becoming entangled in the stroma in the interstitial space.

It was found that concentration of the C/A molecules into tumor tissue is the product of two processes which depend upon chain length.

1. Uptake into tumor tissue by reptation, is a first process in which uptake becomes less effective as the peptide chain increases in length. Even though reptation can allow passage through obstructions and pores, the longer the molecule the more it will be retarded in its passage into tumor interstitium. This process is well known and gives rise to the separation of DNA molecules or denatured proteins in gel electrophoresis.

2. The second process involves clearance of the C/A complex molecules from the blood circulation performed by glomerular filtration of the kidneys. Clearance is rapid for short molecules, resulting in a short plasma lifetime. Plasma lifetime increases rapidly as the peptides increase in length but a plateau is reached for a molecular length of about 500 residues and little further change in lifetime occurs.

The blood circulation times are measured from time of injection with an initial concentration C, until the concentration drops to C/e, where e is the base of the natural logarithm. Plasma lifetimes for Gd-DTPA PLL are known from measurements in this laboratory and from prior art reports. These lifetimes vs. chain length are plotted in FIG. 4.

Model

The concentration of carrier polypeptide molecules within a tumor may be explained by a simple model. The total tumor enhancement in the absence of a significant loss of contrast agent from the tumor can be given as:

$$E(t) = \alpha \, \mu_T \int_0^t e^{-t/\tau} dt$$

Here E(t) is the delivery of C/A molecules to a tumor at a time t, $\alpha$ is a constant relating enhancement to concentration of C/A in tumor, $\mu_T$ is the uptake coefficient into tumor. The exponential function represents a first order process for clearing molecules from the blood circulation, and $\tau$ is the plasma lifetime of the agent in the blood.

Therefore, it follows that the tumor enhancement at some time t after injection of C/A molecules will be given as:

$$E(t) = \alpha \, \mu_T \tau (1 - e^{-t/\tau})$$

which, for $t >> \tau$, becomes $$E(t) = \alpha \, \mu_T \tau.$$

Thus, when there is no loss of contrast agent from the tumor in the time period being measured, and when the blood circulation lifetime is shorter than this time, the delivery of C/A molecules is simply proportional to the product of the uptake coefficient and the blood circulation lifetime $\tau$.

Conformation

An elongated, worm-like conformation of a macromolecule results in greater uptake than other conformations, such as folded, or globular conformations. Conformation may be measured by a persistence length of the molecule. This may be determined by light scattering.

Figure 2:
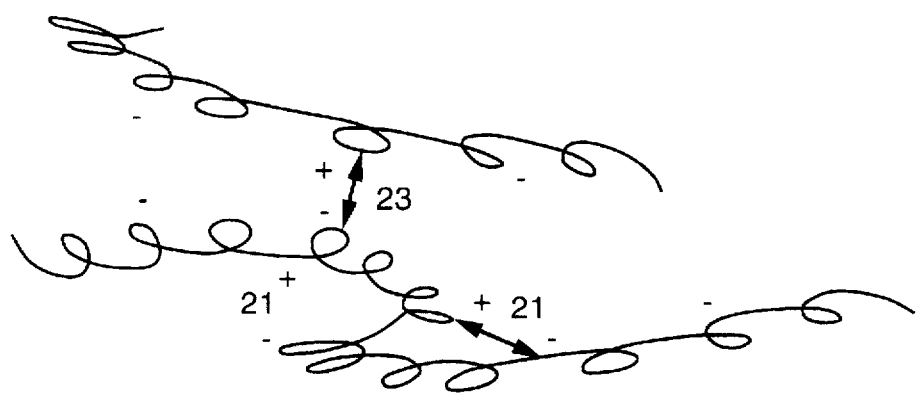
FIG. 2 is an illustration of inter-strand and intra-strand cross-linking of polypeptides.

Conformation is a result of intra-chain charge interaction, and rigidity of the molecule. C/A carrier molecules are selected to be polypeptides. However, many polypeptides tend to fold into tight random coils due to the relatively free rotation around each peptide bond. Also, if each polypeptide is composed of opposite charge amino acids, then intra-chain charge interaction as shown by bond 21 in FIG. 2. Inter-chain charge interaction between chains may also occur as shown by bond 23 of FIG. 2. If there is significant intra-chain charge interactions, the C/A complex molecules may assume a globular, or folded, conformation.

The conformation required by the present invention is that of a worm-like shape being essentially a stretched out, extended chain with little folding. A measure of the "straightness" of a molecule is a persistence length. Persistence length is related to a radius of gyration, measured by light scattering experiments. A folded polypeptide such as poly-L-lysine (PLL) with little or no substitution, has a low persistence length of about 10 Angstroms (Å), and is not suitable for targeting tumor tissue. However, it was found that C/A complex molecules with a persistence lengths of 100–200 Å concentrated much more readily in tumor tissue than C/A complex molecules of PLL. It is also believed that persistence lengths from 100–600 Å would be appropriate for the present invention.

In order to produce a carrier molecule and active agent complex having a proper persistence length, usually one must eliminate or reduce intra-chain charge interactions as well as restrict rotation about a bond at each peptide link.

This may be accomplished by substituting with a steric hindrance molecule extending as side chains off of the main chain.

For example, if the polypeptide carrier is PLL, which has a positive charge at each lysine, one must attach a sufficient amount of substitutions that would impair peptide bond rotation.

One such method is to attach molecules such as diethylene triamine pentaacetic acid (DTPA) at most of the lysine residues. Due to the physical size and the steric hindrance effects of DTPA, there is a physical restraint on peptide bond rotation which extends the peptide into a worm-like configuration. Each of these DTPA molecules is attached at the amine group of a lysine amino acid. The degree of substitution is important in defining the configuration of the overall polypeptide. It was found that substituted PLL works well when it is more than 90% substituted with DTPA.

In the case that the polypeptide has both positively and negatively charged sections along its length, such as a polypeptide composed of positively charged amino acids having a low degree of substitution with a negatively charged entity, there is a large degree of folding. However, by further substitution, the charge interactions are reduced, thereby reducing the degree of folding.

$T_1$ Relaxation

It is sometimes difficult to measure the persistence length of certain molecules by light scattering to determine their conformation because of the effects of contaminant particles in the test solutions. However, it was found that by measuring the magnetic resonance (MR) $T_1$ relaxation of a paramagnetic entity attached to the carrier, one could determine the conformation of the molecules of interest. This is performed by attaching a magnetic resonance (MR) active entity, such as gadolinium, to a carrier molecule extending as a sidechain. Usually this is performed by encapsulating the MR active entity in a chelator, such as DTPA.

When the carrier molecule is in an elongated conformation, the chelator/MR active entity is free to rotate about its attachment point to the main chain, allowing a long $T_1$ relaxation time of the surrounding water protons which are the source of the MR signal.

When the carrier molecule is in a globular or highly folded conformation, steric hindrance, and molecular crowding causes interaction with the chelator/MR active entity restricting rotation about its bond to the main chain. Thus, the chelator/MR active entity moves only with the general slow motion of the carrier molecule. This produces a short $T_1$ relaxation time.

It was therefore found that a high relaxivity is associated with a molecule which folds upon itself into a globular conformation, such as albumen, at about 15 sec.$^{-1}$ milliMolar$^{-1}$ (sec$^{-1}$mM$^{-1}$). A low relaxivity is associated with an elongated molecule such as highly substituted Gd-DTPA PLL$^h$ in which the Gd can rotate rapidly, having a relaxivity of about 8 sec$^{-1}$mM$^{-1}$. The optimum conformation of the present invention is associated with a relaxivity of 7–8 mM$^{-1}$sec.$^{-1}$.

When the relaxivity of a peptide agent was high, the uptake coefficient of such an agent was invariably low, evidently due to the absence of the reptation mechanism. Thus, it was important to establish that the peptides being compared for optimum length were all of the same conformation. Relaxivity values of the Gd-PLL for various lengths were tested to be between 7.5 and 10 for average chain length of 92, 219, 455, 633, and 1163 residues, in a 2 Tesla Magnet (2T) at 80 mHz and 23° C. This suggests that a reasonably uniform conformational state was achieved for the peptides being compared.

Charge

Since many in-vivo chemical entities have a negative charge, molecules introduced into the subject must have a net negative charge to reduce agglutination and to allow for stable long circulation in the blood plasma. It is known that negatively charged dextran molecules undergo glomerular filtration at a much slower rate than equivalent dextran molecules of positive charge or neutral charge.

The high net negative charge is also desirable since it also causes the C/A complex molecules to retain their elongated, worm-like conformation.

Figure 3:
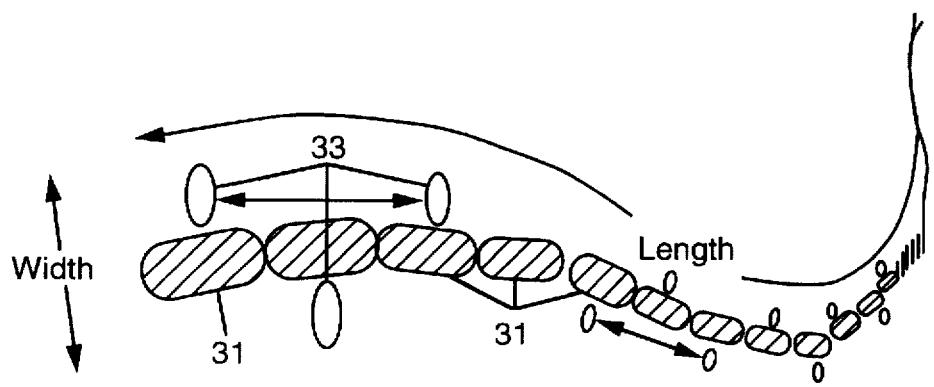
FIG. 3 an illustration of a highly substituted polypeptide according to the present invention.

In FIG. 3 a polypeptide carrier having a plurality of side chains substituting the hydrogen atoms is shown. The polypeptide is comprised of a plurality of amino acids 31, each linked end to end through a polypeptide bond. A plurality of side residues 33 are attached which cause steric hindrances and repulsion to straighten the polypeptide chain.

FIG. 3 also shows that the length of the polypeptide should be significantly longer than its diameter by approximately 2 orders of magnitude. This causes the polypeptide and any attached chemical entities to pass through pores in tumor tissue and become trapped the tumor interstitium as discussed above.

Poly-glutamic and Poly-aspartic Acid

Polypeptides of poly-glutamic acid and poly-aspartic acid are preferred over poly-lysine since the poly-glutamic and poly-aspartic acid contain only negative charges and therefore no attractive charge interactions result when substitutions of DTPA or similar negatively charged molecules are made on these peptides.

A method of creating a poly-glutamic carrier molecule highly substituted with DTPA as a steric hindrance sidechain causing a worm-like configuration of the carrier molecule, and attaching a chemotherapy drug, doxorubicin, is described below.

A mixed anhydride of DTPA was prepared according to the method as described in P. F. Sieving, A. D. Watson, and S. M. Rocklage, *Bioconjugate Chem.* 1. 65–71, (1990).

A flask was charged with 7 ml. acetonitrile and 2.6 g of DTPA. The solution was warmed to 60° C. under a nitrogen atmosphere. Triethylamine was then added via syringe. The mixture was stirred until homogeneous. The clear solution was then cooled to –30° C. under nitrogen atmosphere and then 0.5 ml. of isobutyl chloroformate was slowly added to result in the anhydride of DTPA.

The anhydride of DTPA is then reacted overnight with a diamine (in which the diamine is in large excess to the anhydride). Ethylene diamine is a suitable choice, giving in the end a DTPA linkage of the desired length to achieve proper steric hindrance against peptide chain bending. The product is separated from the diamine and from DTPA which was not reacted, by ion exchange chromatography. The product has an amine group on one of the acetic acid arms of the pentaacetic acid structure of the DTPA Linking this amine-DTPA product to the poly-glutamic acid is done by a carboxyl coupling method. The carboxy acid groups of the poly-glutamic acid are activated by a coupling reagent, 1 Ethyl-3-(3-Dimethylaminopropyl) carbodiimide Hydrochloride (EDC) (Pierce, Rockford, Ill.). The activated group is then combined with the amine modified DTPA to produce an amide linkage of the DTPA to the peptide backbone as a sidechain which acts as a steric hindrance straightening the polypeptide backbone. The end product is separated by diafiltration.

Attaching Doxorubicin

For purposes of therapy, a drug can be attached at a few sites along the substituted polypeptide chain. A drug of choice would be doxorubicin, which has been shown to have activity against solid tumors (see Sezaki and Hashida paper above).

The covalent attachment method could be one of several kinds. One such method is to use the activated carboxy group of a glutamic acid to form an amide bond with an amine group of the doxorubicin.

Even though a specific chemotherapy drug, doxorubicin is mentioned here, any known chemotherapy drugs capable of being attached to the specific polypeptide being used may be employed.

For therapy, one could use a radiotherapieutic agent such as a beta emitters, an isotope of Yttrium, $^{90}$Y, or Astatine, $^{211}$At, which also emits alpha particles.

The active agent may also be used in imaging in addition to the MR imaging mentioned above. By binding a gamma emitter, such as Indium, $^{111}$In, or Gadolinium, $^{153}$Gd to the carrier molecules, gamma camera images may be obtained.

Also, Zirconium, $^{89}$Zr, which is a positron emitter, may be employed in positron emission tomography (PET) imaging.

Also, other types of chelators of similar size to DTPA may be used to provide the steric hindrance against peptide bending and to provide sites for contrast agent attachment as well as for therapeutic agents. One such chelator, 1, 4, 7, 10-tetraazacyclododecane-1, 4, 7, 10-tetraacetic acid (DOTA) may be also employed by a suitable attachment protocol to the peptides in question. Other molecules having the proper steric hindrance which may attach may also be used provided they have a net negative charge.

Since many in vivo molecules tend to have a negative charge, it is advantageous for the C/A complex molecules to also have a net negative charge in order to avoid agglutination with blood plasma proteins. Positively charged molecules are also known to stick to cell surfaces (which are generally negatively charged.

Other polypeptides may also be used such that after the modifications to the initial peptide chain the requirements of cross-sectional diameter, molecular length and persistence length are met. In addition the complex should also have a net negative charge.

EXPERIMENTAL RESULTS

Figure 5:
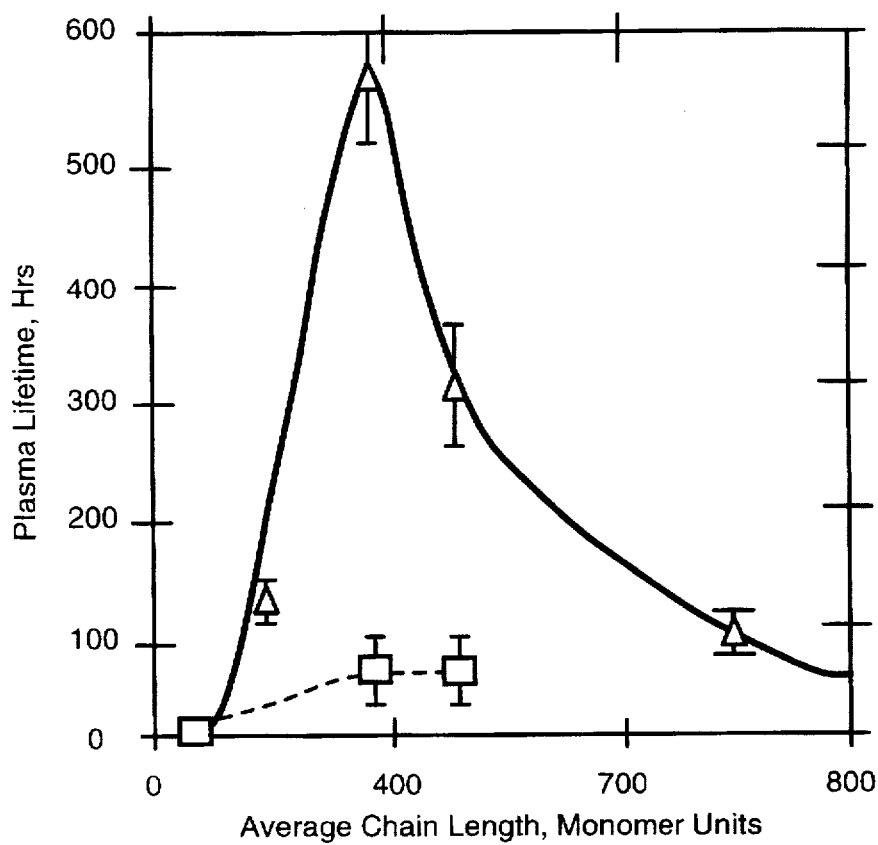
FIG. 5 is graph of tumor enhancement vs. average polymer chain length.

In FIG. 5, tumor enhancement in MR images after 24 hours is plotted against chain length of the injected contrast agent peptides. The injections were given intravenously and the observed enhancements were normalized to a standard dose of contrast agent, that is 0.1 mMole Gd/kG. Since tumor enhancement is directly proportional to C/A concentration within the tumor, this indicates the increased concentration of C/A complex molecules within the tumor. Tumors were from a rat adenocarcinoma cell line grown in Fisher 344 female rats. There is a substantial optimum at around a chain length of 450 residues. The optimum enhancement value of about 600% is much larger than achieved for any contrast agent previously reported.

To put this result of the present invention into perspective, a conventional small molecule agent that is currently used in clinical imaging, Gd-DTPA affords less than 70% enhancement for a standard dose. This small enhancement of tumor contrast is quickly lost over a period of 15 to 30 minutes. Furthermore, enhancement by Gd-DTPA is localized to regions of tumor near vascular points of entry and is not generally seen throughout the volume of the tumor. As the agent diffuses in the tumor the enhancement fades rapidly.

However, the tumor signals observed with a peptide agent, such as Gd-PLL according to the present invention, are bright throughout the tumor and remain that way beyond 48 hours. These agents appear to penetrate the tumor interior completely and remain in the tumor interstitium for an extended period. Therefore, these results are of interest not only for imaging tumors but also for tumor therapy applications as well.

Figure 4:
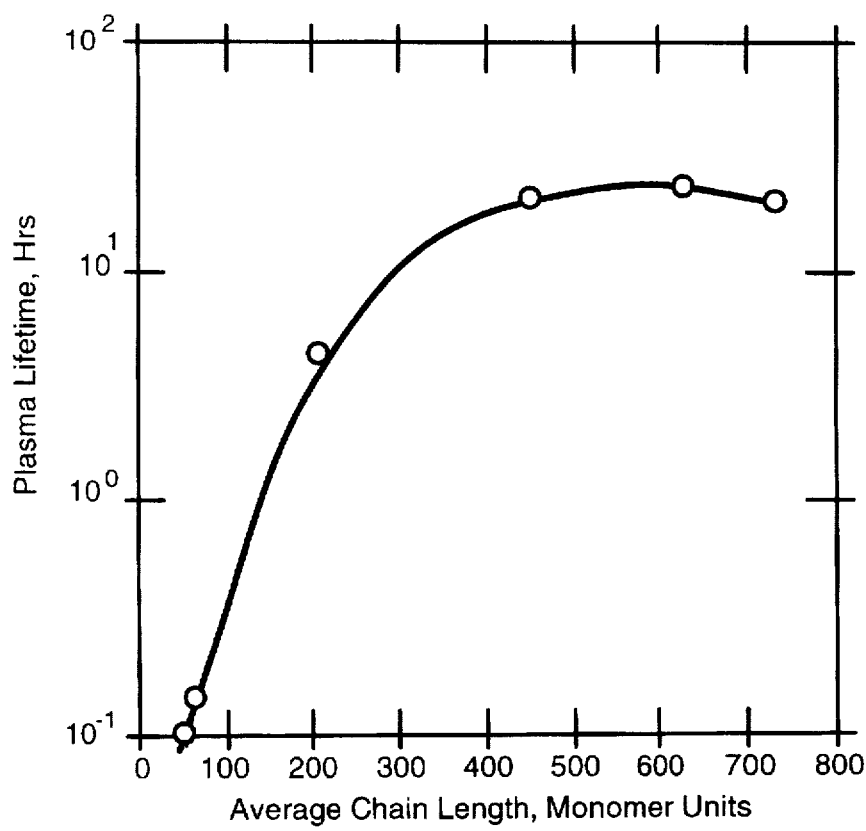
FIG. 4 is graph of plasma lifetime vs. average polymer chain length.

In FIG. 5, the solid line is a fit using the values of τ as shown in FIG. 4 and the expression for E(t) as described in the specification. The dependence of the uptake coefficient, $\mu_T$ on chain length was derived from the enhancements observed for chain lengths of 455, 633, and 1157 monomer units for which the plasma lifetime is not varying very much. The functional dependence on chain length is assumed to hold for the shorter polymer constructs and this assumption yields the indicated fit of enhancement to observed data. The tightly coiled peptide constructs gave enhancements which were very much lower and comparable to observed enhancements with globular proteins: Albumin labeled proteins gave enhancements of approximately 30% and nonspecific monoclonal antibody gave enhancements of 25%, whereas specific antibody gave an enhancement of 48%, as described in Gohr-Rosenthal, S., et. al., "The Demonstration Of Human Tumors On Nude Mice Using Gadolinium-Labeled Monoclonal Antibodies For Magnetic Resonance Imaging" Invest. Rad. 28, 789 (1993).

The tumor enhancements observed for tightly coiled peptides and for globular protein contrast agents are also shown in FIG. 5. The tumor signals for these agents are very much lower. And they are lower not just at 24 hours or 48 hours but for any time after injection.

Independent data on uptake efficiency for peptides is not available. Therefore certain assumptions must be made regarding this parameter. Since the blood plasma lifetime reaches a plateau at a chain length of about 500, it can be assumed that the observed decrease in tumor uptake for chains larger than 450 is entirely due to the decrease in the uptake coefficient. This behavior is extended to smaller chain lengths from the derived functional form of the observed decrease.

The product of this deduced uptake coefficient and the plasma lifetime is given in FIG. 5 as a solid line after normalization to the peak value observed at 450 chain length. It can be seen that this model describes reasonably well the observed enhancement as a function of peptide length.

The tumor uptake of globular proteins and folded peptides is vastly reduced from the optimum uptake of worm-chain peptides as is also shown in FIG. 5 as a dashed line. Evidently the larger molecular size of such molecular conformations greatly restricts their access to the tumor interior. This conclusion is justified because the circulation times of globular proteins and coiled peptides have been measured to be similar to that of worm-chain peptides of the same molecular weight.

Replacing substantially all the lysine residues with DTPA through a mixed anhydride coupling method has the result of stiffening the polypeptide considerably and opening it up into and extended worm-chain configuration. These carrier molecules, designated as GdPLL$^h$, have a radius of gyration of 400 Å and a persistence length of 130 Å. This is very different from the values found for poly-lysine peptide starting material: radius of gyration of 150 Å and a persistence length, $L_p$, of 12Å.

The conformational state is important in trapping and retaining the C/A molecules in the tumor interstitium. In a separate set of experiments with globular proteins and coiled peptides, it was found that these carrier molecules were retained in the tumor after 24 hours. A negatively charged coiled peptide, termed glu:leu, having high negative charge alone was not sufficient for effective tumor targeting, less than 0.3% of the initial dose/gm was retained in the tumor.

A polylysine polypeptide, Gd-PLL$^m$, having substitutions on approximately 50% of the lysines having an intermediate conformation, i.e. not in a fully collapsed tight random coil was also retained relatively poorly compared to GdPLL$^h$ being only at 1–2.5% dose/gm after 24 hours and continuing to decline to a range of 0.5–1.8% dose/gm at 40 hours. Its initial uptake after a few hours is in the range of 5% dose/gm. Thus, in this case, although the complex molecules may get into the tumor reasonably efficiently, they do not remain in the tumor interstitium when the blood level concentration of the C/A complex molecules begin to drop. The tumor levels of the C/A complex molecules using GdPLL$^h$ as a carrier, increase steadily over 24 hours and remain high thereafter for several more days.

Other Embodiments

A useful chemotherapy drug to be attached to the carrier molecule is methotrexate as described in "Site Specific Linkage of Methotrexate to Monoclonal Antibodies Using An Intermediate Carrier" by L. Shih, R. Sharkey, F. James, F. Primus, D. Goldenberg.

Other useful chemotherapy drugs are described in the Sezaki, Hashida paper referenced above. Also, plant and bacterial toxins such as ricin and abrin as described in "Drug-Monoclonal Antibody Conjugates for Cancer Therapy: Potentials and Limitations by M. Primm, in *CRC Critical in Therapeutic Drug Carrier Systems* by CRC Press Vol. 5, Issue 3, 1988 may be used.

While specific embodiments of the invention have been illustrated and described herein, it is realized that modifications and changes will occur to those skilled in the art. It is therefore to be understood that the appended claims are intended to cover all such modifications and changes as fall within the true spirit and scope of the invention.

What we claim is:

1. A method of concentrated delivery of an active agent to a tumor of a subject comprising the steps of:

a) selecting an optimum carrier molecule average length;

b) selecting a carrier molecule having the determined optimum average length, a diameter of between 30–50 Angstroms, a net negative charge, persistence length between 100–600 Angstroms;

c) combining the active agent with the carrier molecule to create a carrier/active agent (C/A) complex molecules; and d) introducing the C/A complex molecules into a blood vessel of said subject to result in reptation and concentrated delivery of said active agent to said tumor of said subject.

2. The method of concentrated delivery of an active agent of claim 1 wherein the step of determining an optimum carrier molecule average length comprises the steps of:

a) acquiring plasma lifetime vs. average chain length data;

b) acquiring tumor uptake vs. average chain length data;

c) multiplying plasma lifetime data by tumor uptake data for corresponding average chain lengths to result in tumor accumulation data;

d) selecting a chain length substantially corresponding to a highest point of the tumor accumulation data.

3. The method of claim 1 wherein the active agent is selected to be an imaging agent.

4. The method of claim 1 wherein the active agent is selected to be a chemotherapy drug.

5. The method of claim 1 wherein the active agent is selected to be a radiotherapy agent.

* * * * *

UNITED STATES PATENT AND TRADEMARK OFFICE
CERTIFICATE OF CORRECTION

PATENT NO. : 5,762,909
DATED : June 9, 1998
INVENTOR(S) : Egidijus Edward Uzgiris It is certified that error appears in the above-identified patent and that said Letters Patent is hereby corrected as shown below:

In the drawings, sheet 3, Figure 5, delete the legend for the vertical axis, and replace it with --Enhancement, % --.

Column 4, line 20, delete "$E(t) = \alpha\mu_r^\tau (1 - e^{-t/\tau})$" and substitute -- $E(t) = \alpha\mu_T\tau(1 - e^{-t/\tau})$ --; and Column 4, line 23, delete "$E(t) = \alpha\mu_r^\tau$" and substitute -- $E(t) = \alpha\mu_T\tau$ --.

Signed and Sealed this

Fifteenth Day of September, 1998

Attest:

BRUCE LEHMAN

*Attesting Officer*   *Commissioner of Patents and Trademarks*